(12) United States Patent
Imagawa et al.

(10) Patent No.: US 10,488,311 B2
(45) Date of Patent: Nov. 26, 2019

(54) RIGIDITY MEASUREMENT APPARATUS AND RIGIDITY MEASUREMENT METHOD

(71) Applicant: Panasonic Intellectual Property Management Co., Ltd., Osaka (JP)

(72) Inventors: Taro Imagawa, Osaka (JP); Akihiro Noda, Nara (JP); Hiroya Kusaka, Hyogo (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 94 days.

(21) Appl. No.: 15/835,806

(22) Filed: Dec. 8, 2017

(65) Prior Publication Data

US 2018/0209883 A1 Jul. 26, 2018

Related U.S. Application Data

(63) Continuation of application No. PCT/JP2017/021087, filed on Jun. 7, 2017.

(30) Foreign Application Priority Data

Jan. 25, 2017 (JP) ................................. 2017-010915

(51) Int. Cl.
*G01M 11/00* (2006.01)
*G01N 3/20* (2006.01)
(Continued)

(52) U.S. Cl.
CPC ................. *G01N 3/20* (2013.01); *G01B 5/04* (2013.01); *G01B 7/16* (2013.01); *G01B 11/16* (2013.01);
(Continued)

(58) Field of Classification Search
CPC ............ G01N 3/20; G01N 3/068; G01N 3/28; G01N 2203/0282; G01B 5/04; G01B 7/16; G01B 11/16; G01M 5/0058; G01M 11/081
(Continued)

(56) References Cited

U.S. PATENT DOCUMENTS 5,146,779 A * 9/1992 Sugimoto ................. G01N 3/40
356/626
6,247,356 B1 * 6/2001 Merck, Jr. ................. G01N 3/42
73/82
(Continued)

FOREIGN PATENT DOCUMENTS

JP 2000-055776 2/2000

OTHER PUBLICATIONS

International Search Report of PCT application No. PCT/JP2017/021087 dated Aug. 29, 2017.

*Primary Examiner* — Max H Noori
(74) *Attorney, Agent, or Firm* — Wenderoth, Lind & Ponack, L.L.P.

(57) ABSTRACT

A rigidity measurement apparatus is a rigidity measurement apparatus that measures rigidity of an object to be measured and includes a load estimator, a displacement calculator, and a rigidity calculator. The load estimator estimates a load applied to a measurement point set on the object to be measured by using a captured image of the object to be measured. The displacement calculator calculates a displacement of the measurement point by using the captured image. The rigidity calculator calculates the rigidity of the object to be measured by using the load and the displacement.

16 Claims, 18 Drawing Sheets

(51) Int. Cl.
*G01M 11/08* (2006.01)
*G01N 3/28* (2006.01)
*G01N 3/06* (2006.01)
*G01B 7/16* (2006.01)
*G01B 5/04* (2006.01)
*G01B 11/16* (2006.01)
*G01M 5/00* (2006.01)

(52) U.S. Cl.
CPC ........ *G01M 5/0058* (2013.01); *G01M 11/081* (2013.01); *G01N 3/068* (2013.01); *G01N 3/28* (2013.01); *G01N 2203/0023* (2013.01); *G01N 2203/0282* (2013.01); *G01N 2203/0647* (2013.01)

(58) Field of Classification Search
USPC .......................................................... 73/854
See application file for complete search history.

(56) References Cited

U.S. PATENT DOCUMENTS

2011/0208038 A1* 8/2011 Konofagou ............ A61B 5/055
600/410
2013/0255362 A1* 10/2013 Takemura ................ G01N 3/42
73/81

* cited by examiner

FIG. 8

|  | Frame 1 | Frame 2 | Frame 3 | ... | Frame n |
|---|---|---|---|---|---|
| 501 | (000,000) | (001,000) | (000,001) | ... | |
| 502 | (000,000) | (001,-001) | (002,000) | ... | |
| 503 | (000,000) | (004,-002) | (006,-004) | ... | |
| 504 | (000,000) | | | ... | |
| 505 | (000,000) | | | ... | |
| 506 | (000,000) | | | ... | |
| 507 | (000,000) | | | ... | |
| 508 | (000,000) | | | ... | |
| 509 | (000,000) | | | ... | |
| 510 | (000,000) | | | ... | |
| 511 | (000,000) | | | ... | |

RIGIDITY MEASUREMENT APPARATUS AND RIGIDITY MEASUREMENT METHOD

TECHNICAL FIELD

The present disclosure relates to a rigidity measurement apparatus and a rigidity measurement method for measuring rigidity of an object to be measured.

BACKGROUND ART

Unexamined Japanese Patent Publication No. 2000-55776 discloses a method for measuring bending rigidity of a structure. According to this method, bending rigidity of an object to be measured can be obtained by disposing a plurality of vibration sensors on the object to be measured, giving impact to the object to be measured, and then calculating propagation velocities of vibrations obtained by the vibration sensors.

SUMMARY OF THE INVENTION

The present disclosure provides a rigidity measurement apparatus that makes it possible to measure rigidity of an object to be measured easily at low cost by using a captured image of the object to be measured.

A rigidity measurement apparatus according to the present disclosure is a rigidity measurement apparatus that measures rigidity of an object to be measured and includes a load estimator, a displacement calculator, and a rigidity calculator. The load estimator estimates a load applies to a measurement point set on an object to be measured by using a captured image of the object to be measured. The displacement calculator calculates a displacement of the measurement point by using the captured image. The rigidity calculator calculates rigidity of the object to be measured by using the load and the displacement.

A rigidity measurement method according to the present disclosure is a rigidity measurement method for measuring rigidity of an object to be measured and includes estimating a load, calculating a displacement, and calculating rigidity. In the estimating the load, a load applied to a measurement point set on an object to be measured is estimated by using a captured image of the object to be measured. In the calculating the displacement, a displacement of the object to be measured is calculated by using the captured image. In the calculating the rigidity, rigidity of the object to be measured is calculated by using the load and the displacement.

A rigidity measurement apparatus and a rigidity measurement method according to the present disclosure make it possible to measure rigidity of an object to be measured easily at log cost by using a captured image of the object to be measured.

BRIEF DESCRIPTION OF DRAWINGS

FIG. 8 illustrates an example of displacements calculated by a displacement calculator.

DESCRIPTION OF EMBODIMENTS

Hereinafter, exemplary embodiments will be described in detail with reference to the drawings as appropriate. However, detailed description beyond necessity may be omitted. For example, detailed description of a matter that has been already known well or repeated description of substantially the same configuration may be omitted. Such omissions are aimed to prevent the following description from being redundant more than necessary, and to help those skilled in the art easily understand the following description.

It should be noted that the attached drawings and the following description are provided for those skilled in the art to fully understand the present disclosure, and are not intended to limit the subject matter as described in the appended claims.

First Exemplary Embodiment

A first exemplary embodiment is described with reference to FIGS. 1 through 15D.

[1-1. Configuration]
[1-1-1. Capturing of Object to be Measured]

Figure 1:
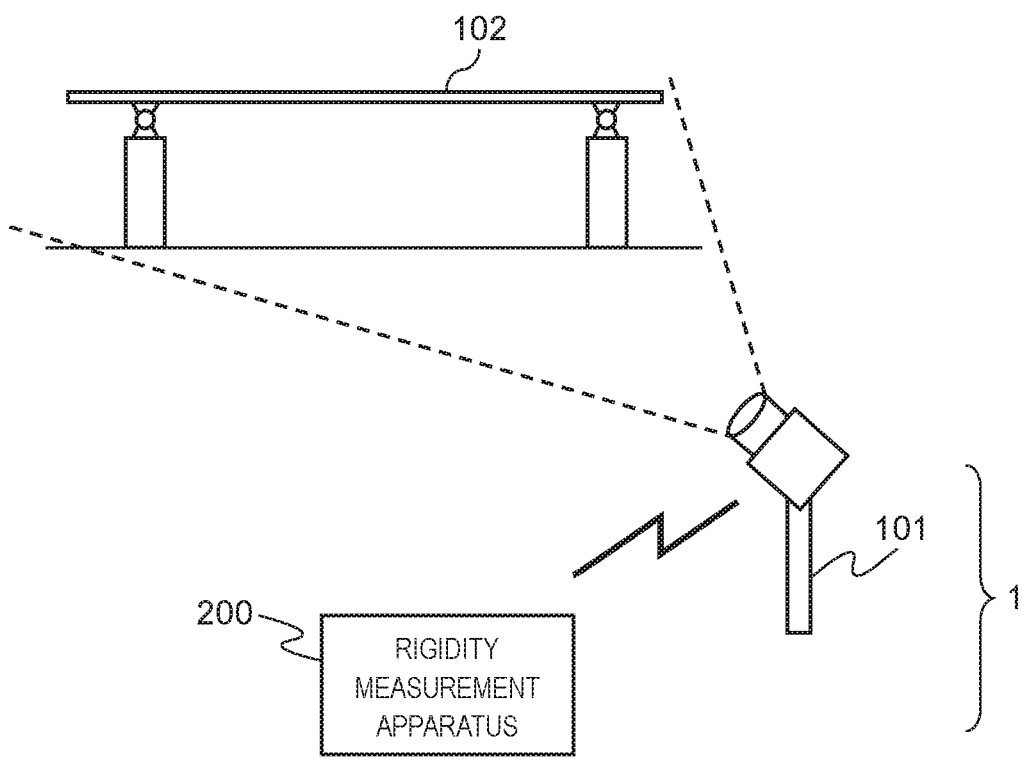
FIG. 1 is an appearance view illustrating an example of a configuration of a rigidity measurement system according to a first exemplary embodiment.

FIG. 1 is an appearance view illustrating an example of a configuration of rigidity measurement system 1 according to the first exemplary embodiment. Rigidity measurement system 1 includes camera 101 and rigidity measurement apparatus 200. Camera 101 captures bridge 102 plural times within a predetermined period and thus generates a plurality of captured images of bridge 102. Camera 101 captures bridge 102 plural times, for example, at predetermined time intervals.

The plurality of captured images generated by camera 101 are supplied to rigidity measurement apparatus 200. Rigidity measurement apparatus 200 calculates a rigidity distribution indicative of a spatial distribution of rigidity of whole bridge 102 from the plurality of captured images input. In the present exemplary embodiment, a case where camera 101 is used as an imaging device and bridge 102 is used as an object to be measured is described as an example.

[1-1-2. Configuration of Rigidity Measurement Apparatus]

Figure 2:
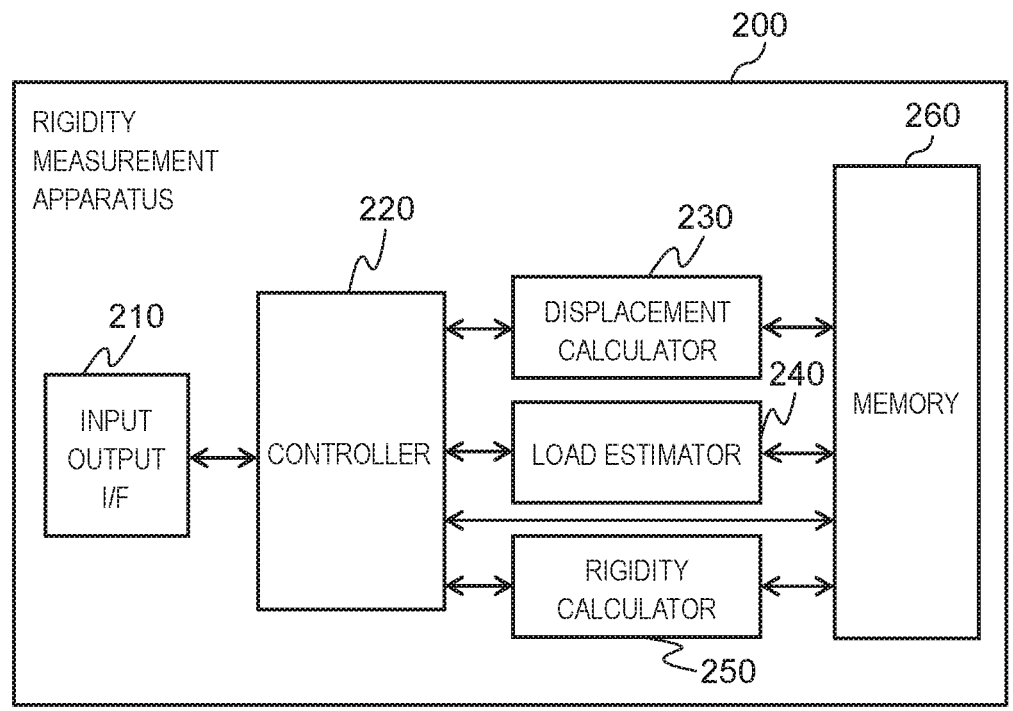
FIG. 2 is a block diagram illustrating an example of a configuration of the rigidity measurement apparatus according to the first exemplary embodiment.

FIG. 2 is a block diagram illustrating an example of a configuration of rigidity measurement apparatus 200 according to the first exemplary embodiment. As illustrated in FIG. 2, rigidity measurement apparatus 200 includes input output I/F 210, controller 220, displacement calculator 230, load estimator 240, rigidity calculator 250, and memory 260. Rigidity measurement apparatus 200 has, for example, a non-volatile memory in which a program is stored, a volatile memory that is a temporary storage region for execution of the program, an input output port, and a processor that executes the program.

Input output I/F 210 receives input of the plurality of captured images of bridge 102 captured within a predetermined period. Input output I/F 210 outputs a rigidity distribution (rigidity values at a plurality of measurement points and a state of distribution of the rigidity values) of bridge 102 calculated by rigidity calculator 250. Input output I/F 210 receives input of the plurality of captured images generated by camera 101, for example, wirelessly, through a wire, or through a recording medium. Then, input output I/F 210 stores the plurality of captured images in memory 260. Furthermore, input output I/F 210 supplies the rigidity distribution of bridge 102 calculated by rigidity calculator 250, for example, to a display (not illustrated), for example, wirelessly, through a wire, or through the recording medium. The display displays the rigidity distribution supplied from rigidity measurement apparatus 200.

Controller 220 controls an operation of each unit of rigidity measurement apparatus 200.

Displacement calculator 230 calculates a displacement of a measurement point set on an object to be measured by using a captured image of the object to be measured. More specifically, displacement calculator 230 detects bridge 102 in each of the plurality of captured images generated by camera 101, which are stored in memory 260. Then, displacement calculator 230 calculates spatial displacements at a plurality of measurement points set on bridge 102. Displacement calculator 230 thus calculates a displacement distribution (displacement amounts of the plurality of measurement points and a state of distribution of the displacement amounts) of bridge 102. Then, displacement calculator 230 stores the displacement distribution in memory 260.

Load estimator 240 estimates a load applied to a measurement point set on an object to be measured by using a captured image of the object to be measured. More specifically, load estimator 240 detects a load source on bridge 102 in each of a plurality of captured images stored in memory 260. After detecting the load source such as a vehicle that applies a load on bridge 102, load estimator 240 detects a kind of load source and a position of the load source on bridge 102. Then, load estimator 240 acquires a load value corresponding the kind of load source that is stored in advance in memory 260. Alternatively, a load source that applies a load on bridge 102 may be determined in advance, and load estimator 240 may acquire a predetermined load value that is stored in advance in memory 260. Specifically, in a case where a load source is fixed to a crane truck, load estimator 240 may acquire a load value of a crane truck stored in memory 260. In this case, each unit of rigidity measurement apparatus 200 performs processing by using only a captured image including a crane truck. Load estimator 240 calculates a load distribution indicative of a spatial distribution of a load applied to bridge 102 by using the position of the load source and the acquired load value.

In a case where a measurement point and the position of the load source match, load estimator 240 may use a load value stored in memory 260 as a load applied to the measurement point when estimating the load applied to the measurement point. In a case where a measurement point and the position of the load source do not match, load estimator 240 may estimate a load applied to the measurement point in accordance with a distance between the measurement point and the position of the load source and the load value stored in memory 260.

Rigidity calculator 250 calculates a rigidity distribution indicative of a spatial distribution of rigidity on an object to be measured by using a displacement distribution and a load distribution. Specifically, rigidity calculator 250 calculates a rigidity distribution of bridge 102 by using a displacement distribution calculated by displacement calculator 230 and a load distribution calculated by load estimator 240. Then, rigidity calculator 250 stores the rigidity distribution in memory 260.

Memory 200 stores captured images supplied froth input output I/F 210. Furthermore, memory 260 is used as a work memory for each unit. For example, memory 260 stores a displacement and a displacement distribution calculated by displacement calculator 230. Memory 260 stores a load distribution calculated by load estimator 240 or load values for respective kinds of load sources such as a vehicle. Memory 260 stores a rigidity distribution of bridge 102 calculated by rigidity calculator 250. Memory 260 is configured, for example, with a semiconductor storage element that is capable of operating at a high speed such as a dynamic random access memory (DRAM).

All or part of functions of rigidity measurement apparatus 200 is achieved, for example, by execution of a program stored in the non-volatile memory by the processor.

[1-1-3. Another Configuration of Rigidity Measurement Apparatus]

Bridge 102 is not always located at a same position in a plurality of captured images generated by camera 101. In such a case, an error occurs in a displacement calculated by displacement calculator 230. The rigidity measurement apparatus may have a function of correcting the displacement calculated by displacement calculator 230 in order to deal with this error.

Figure 3:
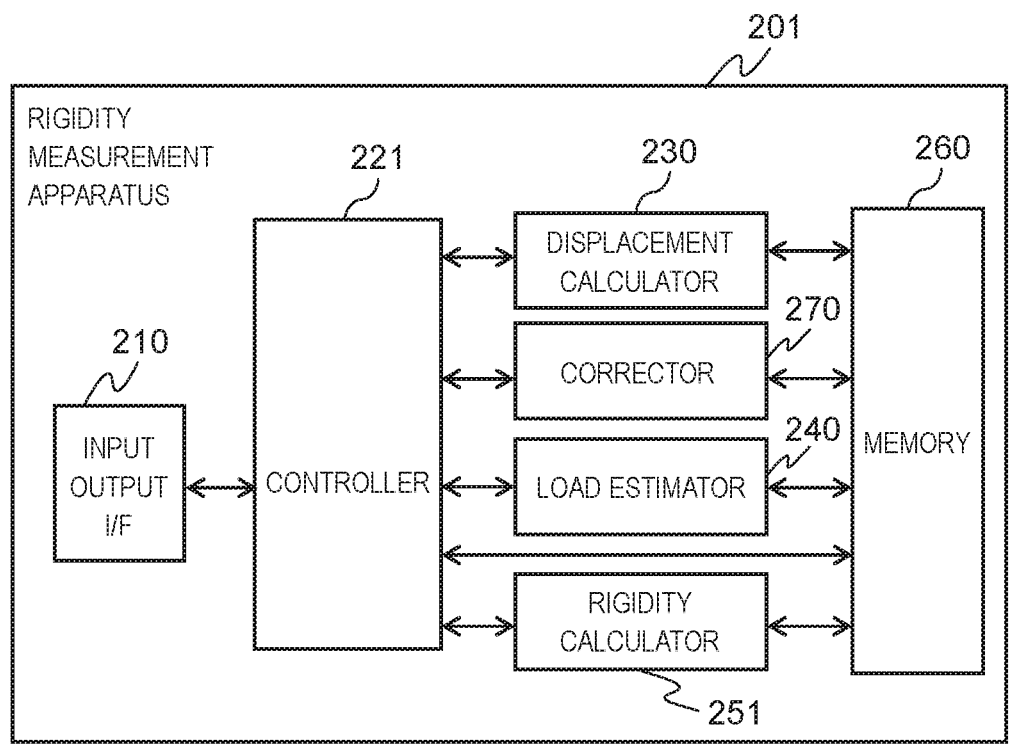
FIG. 3 is a block diagram illustrating another example of a configuration of the rigidity measurement apparatus according to the first exemplary embodiment.

FIG. 3 is a block diagram illustrating another configuration of the rigidity measurement apparatus according to the first exemplary embodiment. In rigidity measurement apparatus 201 of FIG. 3, constituent elements that perform identical operations to those of rigidity measurement apparatus 200 of FIG. 2 are given identical reference signs and are not described repeatedly.

Controller 221 controls an operation of each unit of rigidity measurement apparatus 201.

Rigidity measurement apparatus 201 includes corrector 270. Corrector 270 corrects displacements of a plurality of measurement points calculated by displacement calculator 230 by using a displacement (reference displacement) of a predetermined reference measurement point calculated by displacement calculator 230. More specifically, corrector 270 corrects displacements of measurement points other than the predetermined reference measurement point set on bridge 102 in a captured image by using a reference displacement of the predetermined reference measurement point as a reference. Corrector 270 thus corrects a displacement distribution. Then, corrector 270 stores the corrected displacement distribution in memory 260. The reference measurement point is, for example, a point that is assumed to be displaced by a smallest amount among the plurality of measurement points.

Rigidity calculator 251 calculates a rigidity distribution from a displacement distribution corrected by corrector 270 and a load distribution calculated by load estimator 240. Then, rigidity calculator 251 stores the rigidity distribution in memory 260.

[1-2. Operation]

[1-2-1. Operation without Correction]

Figure 4:
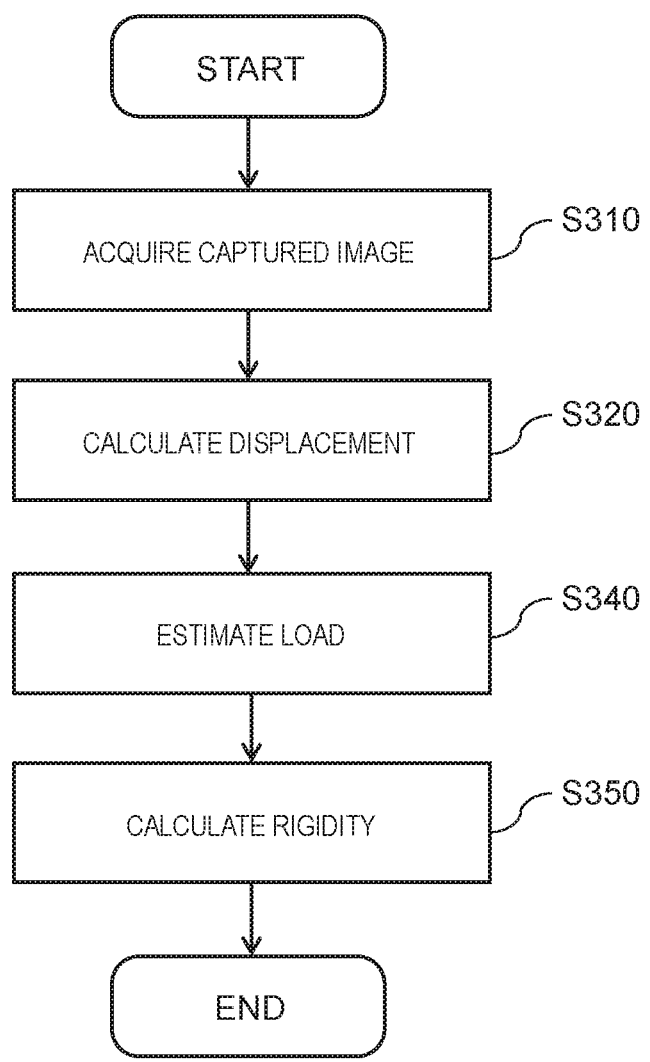
FIG. 4 is a flow chart illustrating an operation of the rigidity measurement apparatus according to the first exemplary embodiment.

FIG. 4 is a flowchart illustrating an operation of rigidity measurement apparatus 200 according to the first exemplary embodiment.

(Captured Image Acquisition Step S310)

Controller 220 acquires captured images via input output I/F 210. The captured images are images of bridge 102 captured within a predetermined period by camera 101. Controller 220 stores the acquired captured images in memory 260.

(Displacement Calculation Step S320)

Controller 220 causes displacement calculator 230 to calculate temporal displacement at a plurality of measurement points set on bridge 102. In particular, in a case where bending rigidity that will be described later is calculated, displacement calculator 230 calculates displacements of three or more measurement points. Displacement calculator 230 takes out the plurality of captured images stored in memory 260 in order of photographing time and calculates a displacement of bridge 102 for each of the captured images. Displacement calculator 230 calculates a displacement distribution from the calculated displacement. Then, displacement calculator 230 stores the displacement distribution in memory 260.

(Load Estimation Step S340)

Controller 220 causes load estimator 240 to calculate a load distribution of bridge 102. Load estimator 240 recognizes a kind and a position of a load source (e.g., a vehicle) from the captured images stored in memory 260 by image recognition. For example, in a case where the load source is a vehicle, load estimator 240 recognizes a kind of vehicle and a running position of the vehicle on bridge 102. Load estimator 240 acquires a load value corresponding to the recognized kind of load source among load values for respective kinds that are stored in advance in memory 260. Load estimator 240 calculates a spatial load distribution by using the load value and the position of the load source. Then, load estimator 240 stores the load distribution in memory 260. Load estimator 240 may acquire a load value not from memory 260 but from an external database via I/F 210. In a case where a kind of load source is determined in advance, load estimator 240 may detect only a position of the load source and use a predetermined load value stored in memory 260 in advance as a corresponding load value.

(Rigidity Calculation Step S350)

Controller 220 causes rigidity calculator 250 to calculate a rigidity distribution of whole bridge 102 by using the displacement distribution calculated by displacement calculator 230 and the load distribution calculated by load estimator 240. Rigidity calculator 250 reads out the displacement distribution and the load distribution stored in memory 260 and calculates the rigidity distribution of whole bridge 102. Then, rigidity calculator 250 stores the rigidity distribution in memory 260. Controller 220 outputs the rigidity distribution of whole bridge 102 stored in memory 260 via input output I/F 210.

Although the steps are described in order of displacement calculation step S320 and then load estimation step S340 in FIG. 4, the steps may be performed in order of load estimation step S340 and then displacement calculation step S320. In this case, displacement calculation step S320 can be suspended while no load source is present.

[1-2-2. Operation with Correction]

Figure 5:
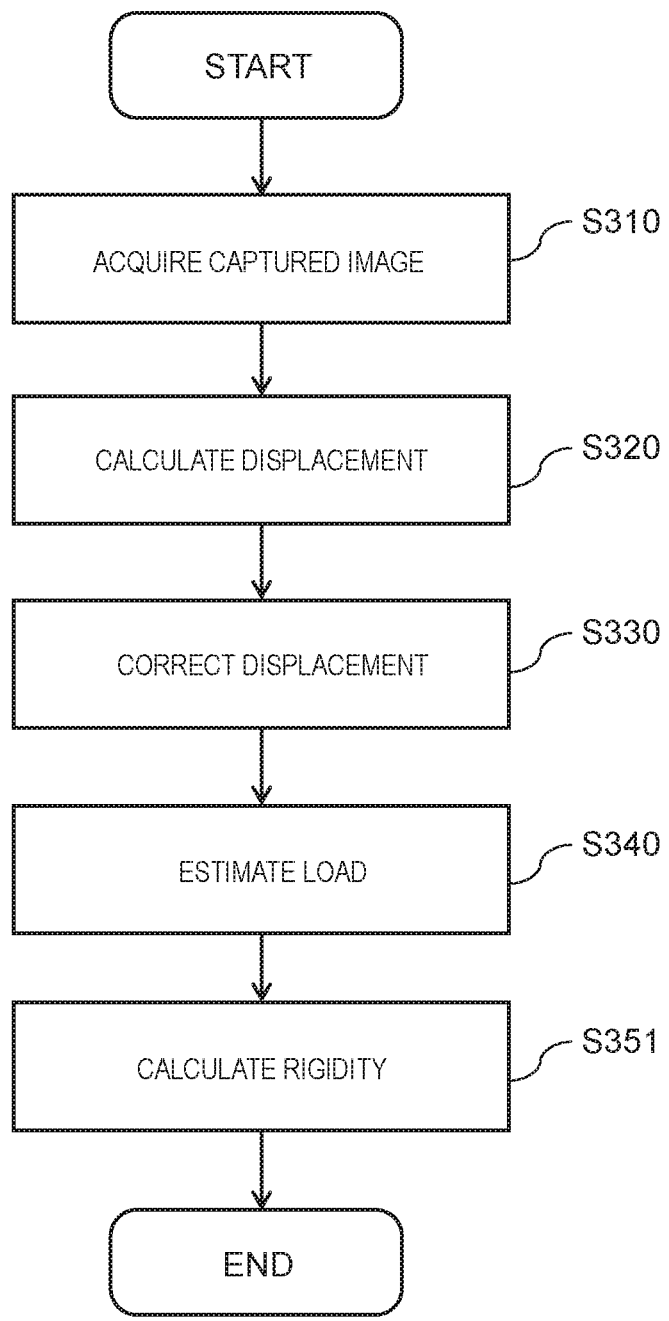
FIG. 5 is a flowchart illustrating another operation of the rigidity measurement apparatus according to the first exemplary embodiment.

FIG. 5 is a flowchart illustrating another operation of the rigidity measurement apparatus according to the first exemplary embodiment. FIG. 5 illustrates an operation of rigidity measurement apparatus 201.

In FIG. 5, steps in which identical operations to those in the flowchart of FIG. 4 are performed are given identical reference signs and are not described repeatedly.

(Displacement Correction Step S330)

Controller 221 causes corrector 270 to correct displacements at a plurality of measurement points calculated by displacement calculator 230. Corrector 270 reads out temporal displacements at the plurality of measurement points stored in memory 260 and corrects each displacement by using a reference displacement. Corrector 270 stores the corrected displacements in memory 260.

(Rigidity Calculation Step S351)

Controller 221 causes rigidity calculator 251 to calculate a rigidity distribution by using a displacement distribution at the plurality of measurement points corrected by corrector 270 and a load distribution calculated by load estimator 240. Rigidity calculator 251 reads out the displacement distribution and the load distribution at the plurality of measurement points stored in memory 260 and calculates the rigidity distribution. Rigidity calculator 251 stores the calculated rigidity distribution in memory 260.

The processes in displacement correction step S330 and rigidity calculation step S351 may be different procedures that are mathematically equivalent or may be collectively performed as a unified procedure as a result.

[1-2-3. Operation Example 1]

An example of an operation of rigidity measurement apparatus 201 is described herein.

Controller 221 acquires a plurality of captured images of bridge 102 via input output I/F 210 as illustrated in FIG. 1. Controller 221 stores the plurality of captured images in memory 260.

Figure 6A:
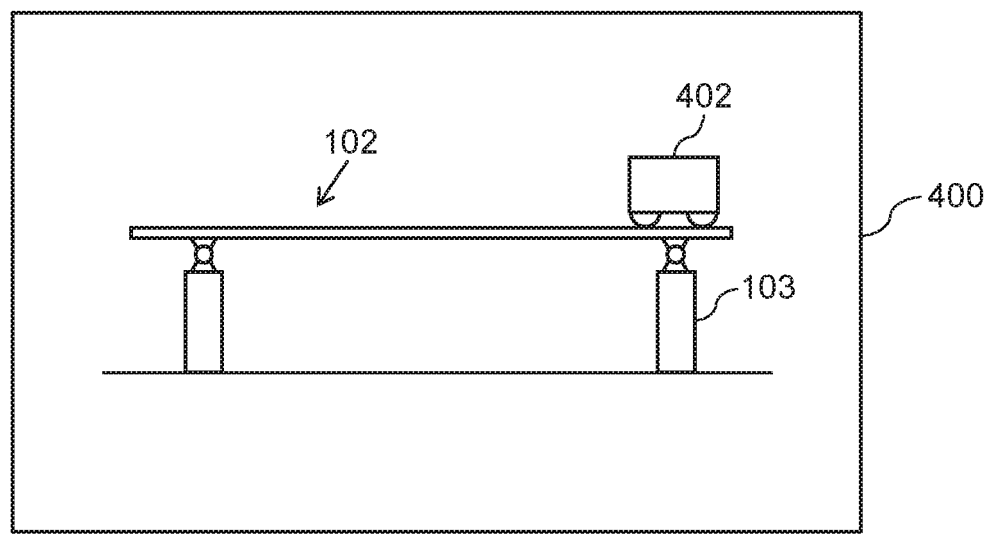
FIG. 6A illustrates an example of a captured image of a bridge.
Figure 6B:
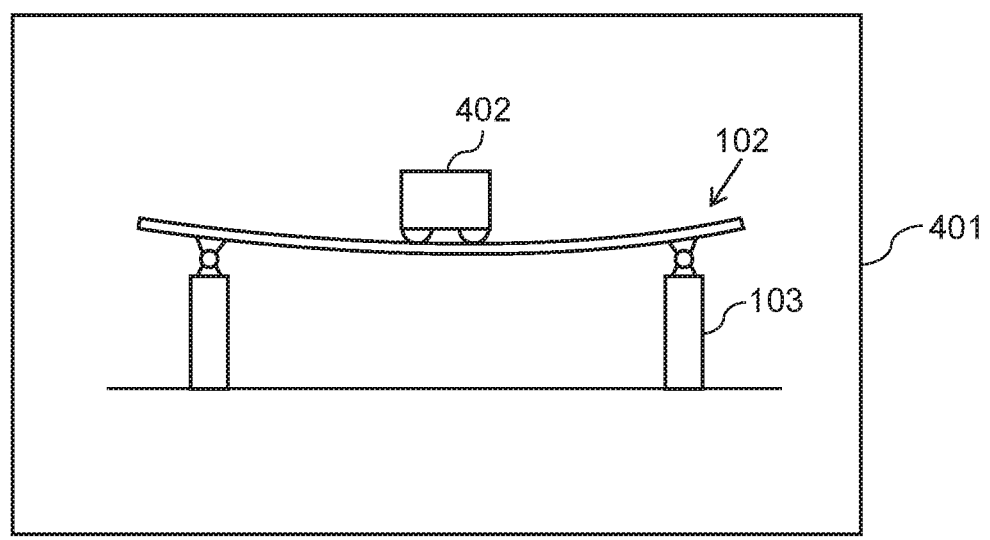
FIG. 6B illustrates another example of the captured image of the bridge.

FIG. 6A illustrates an example of a captured image of bridge 102. FIG. 6B illustrates another example of the captured image of bridge 102. Captured image 400 illustrated in FIG. 6A and captured age 401 illustrated in FIG. 6B are images of bridge 102 that are captured at different times. Captured images 400 and 401 show that vehicle 402 that is a load source is present on bridge 102. In captured image 400, vehicle 402 is present on bridge support 103 for bridge 102, and bridge 102 is not displaced. Meanwhile, in captured image 401, vehicle 402 is located close to a center of bridge 102, and bridge 102 is displaced. As described above, an object (e.g., vehicle 402) different from bridge 102 may be eluded in a captured image.

Displacement calculator 230 detects bridge 102 present in the captured image by using an existing image recognition technology. Displacement calculator 230 detects coordinates of a plurality of measurement points set on detected bridge 102.

Figure 7:
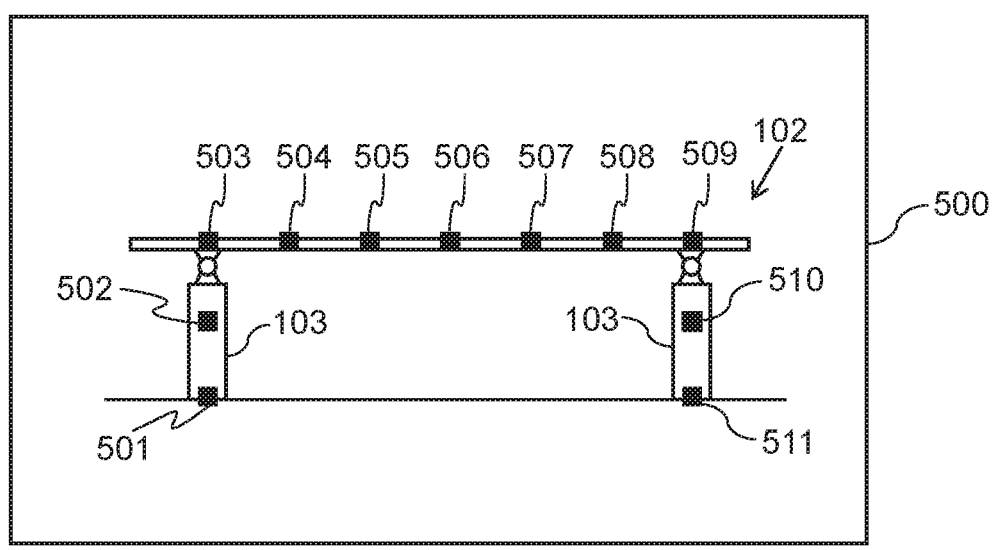
FIG. 7 illustrates an example of a way in which measurement points set on a bridge are disposed.

FIG. 7 illustrates an example of a way in which the plurality of measurement points set on bridge 102 are disposed.

In FIG. 7, measurement points 501 through 511 are the plurality of measurement points set on bridge 102. The measurement points may be set in advance by a user or may be set after bridge 102 is automatically detected by image recognition. In FIG. 7, the measurement points are set at almost regular intervals, but the effects of the present exemplary embodiment can be obtained even in a case where the measurement points are set at irregular intervals. In the present exemplary embodiment, at least one of the plurality of measurement points is set as a reference measurement point. It is assumed here that the reference measurement point is a measurement point that is affected by a load or the like least and is less displaced than other measurement points. In the first exemplary embodiment, measurement point 501 and measurement point 511 are used as the reference measurement points. Measurement point 501 and measurement point 511 are set close to points of contact between bridge supports 103 of bridge 102 and substructures (not illustrated) placed in ground that support bridge supports 103.

Displacement calculator 230 takes out the plurality of captured images stored in memory 260 in order of photographing time and calculates a displacement of bridge 102 for each of the captured images. Displacement calculator 230 calculates a displacement at each measurement point, for example, between image 400 and image 401. Displacement calculator 230 can use block matching or a correlation method as a method for calculating a displacement in captured images. Examples of the correlation method include a normalized cross correlation method, a phase correlation method, and a laser speckle correlation method. Furthermore, displacement calculator 230 may use a general displacement calculation method such as a sampling moire method or a feature point tracking method. Accuracy of displacement calculation may be pixel-order accuracy or may be subpixel-order accuracy.

FIG. 8 illustrates an example of displacements calculated by displacement calculator 230. FIG. 8 illustrates position coordinates (x, y) of measurement points 501 through 511 in a plurality of captured images (Frame 1, Frame 2, Frame 3, . . . , Frame n) of bridge 102 captured within a predetermined period.

Position coordinates (x, y) of i-th measurement point Pi in captured image Frame t of bridge 102 captured at time t are expressed as Pi(x, y, t). A displacement of i-th measurement point Pi in Frame t is expressed as Di(x, y, t). Displacement Di(x, y, t) is a difference in position coordinates Pi of the measurement point between captured images. In the present exemplary embodiment, i is an integer in a range from 1 to 11. Measurement points P1 through P11 correspond to measurement points 501 through 511.

For example, displacement Di(x, y, t) can be calculated by formula 1 by using position coordinates Pi in a plurality of captured images that are temporally adjacent.

$$Di(x,y,t)=Pi(x,y,t)-Pi(x,y,t-1)$$ [Formula 1]

Alternatively, displacement Di(x, y, t) may be calculated by formula 2 by using position coordinates Pi in a reference captured image and each captured image. The reference captured image is, for example, a captured image that is top in chronological order or an image of an object to be measured that can be regarded as being in a steady state.

$$Di(x,y,t)=Pi(x,y,t)-Pi(x,y,1)$$ [Formula 2]

In formula 2, Pi(x, y, 0) are position coordinates in the reference captured image.

Controller 221 corrects image distortion of an imaging optical system of camera 101 as needed. Controller 221 (an example of a scaling unit) may perform scale correction of a displacement calculated by displacement calculator 230 based on a distance between a measurement point and camera 101 that captures bridge 102. The scale correction is correction for making a ratio of a displacement on a captured image to a displacement in an actual space at one measurement point equal to a ratio of a displacement on a captured image to a displacement in an actual space at another measurement point. Such correction may be performed on a captured image or may be performed on a calculated displacement. Controller 221 may perform the scale correction, for example, by using coordinates, in an actual space, of the measurement points stored in memory 260.

Corrector 270 reads out displacement Di(x, y, t) of each of the measurement points stored in memory 260. Corrector 270 corrects each displacement Di by using displacement D1(x, y, t) of predetermined reference measurement point P1 (measurement point 501) among the plurality of measurement points. That is, corrector 270 subtracts, for each captured image, displacement D1(x, y, t) of the reference measurement point from displacement Di(x, y, t) of each of the measurement points. This makes it possible to eliminate influence of an image displacement that occurs in a case where x and y directions of camera 101 change during shooting.

Furthermore, corrector 270 may set reference measurement point P11 (measurement point 511) different from reference measurement point P1 and perform rotational transform of x and y coordinate values of displacement Di(x, y, t) of each measurement point about the position of reference measurement point P1 such that the value of displacement D11(x, y, t) of reference measurement point P11 becomes close to 0. This makes it possible to eliminate influence of a displacement of each captured image that occurs in a case where a roll direction of camera 101 changes during shooting. Corrector 270 stores the corrected displacements at the measurement points in memory 260.

The reference measurement point may be set on bridge 102 or may be set on an object other than bridge 102. For example, the reference measurement point may be set on a still object (e.g., a building) in background of a captured image. The number of reference measurement points may be increased, and amounts of parallel movement correction and rotation correction x and y directions of each calculation position may be optimized such that a sum of displacements of the reference measurement points becomes minimum. This makes it possible to reduce influence on displacement calculation caused by rotation or a change of directions of camera 101 during shooting. Alternatively, dominant motion (global motion) of a whole image may be detected by analyzing motion of frame images at a plurality of times, and a point in the image that follows this motion may be used as a reference measurement point.

In a case where it is anticipated that a displacement in a captured image caused, for example, by a direction or rotation of camera 101 is within an allowable range, correction of the displacement by corrector 270 may be omitted.

Figure 9:
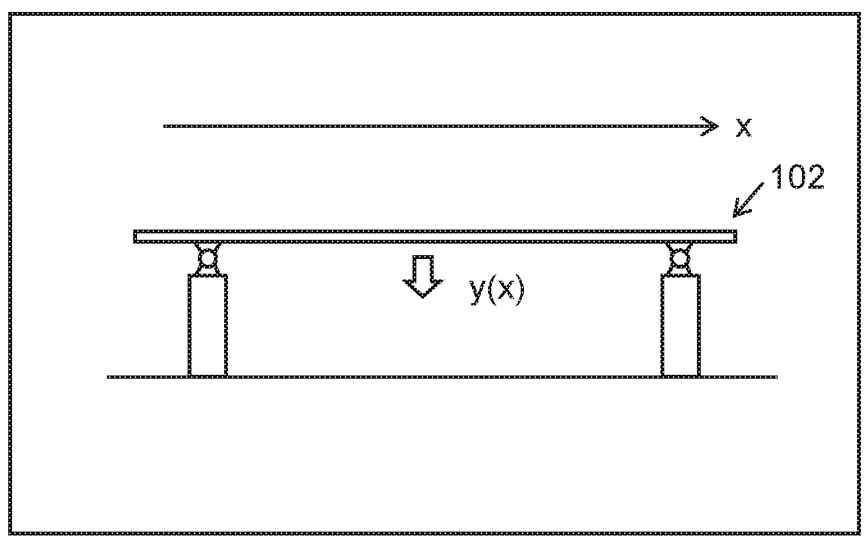
FIG. 9 illustrates a coordinate set on the bridge.

FIG. 9 illustrates a coordinate set on bridge 102. FIG. 9 illustrates a relationship between displacement distribution y(x) and position x used in the following description. As illustrated in FIG. 8, the following description focuses especially on a displacement distribution in a y direction of a bridge beam part among displacements obtained from the respective measurement points of bridge 102.

Load estimator 240 recognizes a kind (a vehicle type in a case of a vehicle) and a position of a load source (e.g., a vehicle) by using captured images stored in memory 260 by image recognition. Load estimator 240 calculates a spatial load distribution by referring to the vehicle type recognition result and load values for respective vehicle types stored in advance in memory 260. Then load estimator 240 stores the load distribution in memory 260. Load estimator 240 may recognize a vehicle type or a specific vehicle by using machine learning. Furthermore, load estimator 240 recognizes a position of a vehicle in a captured image. As the machine learning, template learning, vector quantization, decision tree, neural network, Bayesian learning, or the like can be used. In a case where a vehicle type is determined in advance, it is only necessary to recognize only a position of a vehicle. Load estimator 240 may use, for image recognition, an identifier that has directly learned a relationship between a vehicle image and a vehicle weight.

Load estimator 240 may acquire a load distribution obtained, for example, from another sensor placed on an object to be measured via input output I/F 210.

Figure 10:
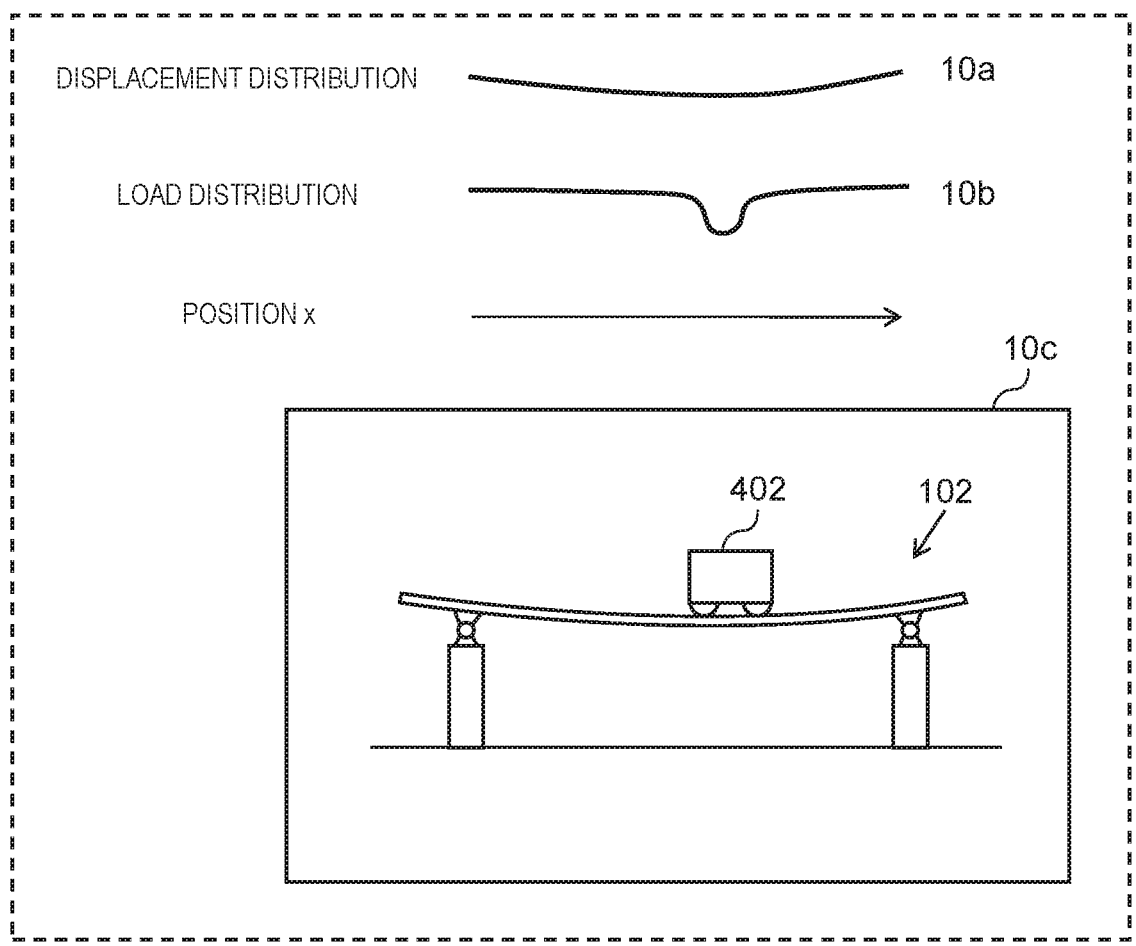
FIG. 10 illustrates an example of a displacement distribution and a load distribution of the bridge.

FIG. 10 illustrates an example of a displacement distribution and a load distribution of the bridge. In FIG. 10, image 10c is a captured image, and displacement distribution 10a and load distribution 10b are a displacement distribution and a load distribution obtained for captured image 10c, respectively. In captured image 10c, vehicle 402 is located close to a center of bridge 102, and bridge 102 is displaced. In this case, displacement distribution 10a shows that a portion where vehicle 402 is located is displaced most. Furthermore, load distribution 10b shows that a load is applied to the portion where vehicle 402 is located.

Figure 11:
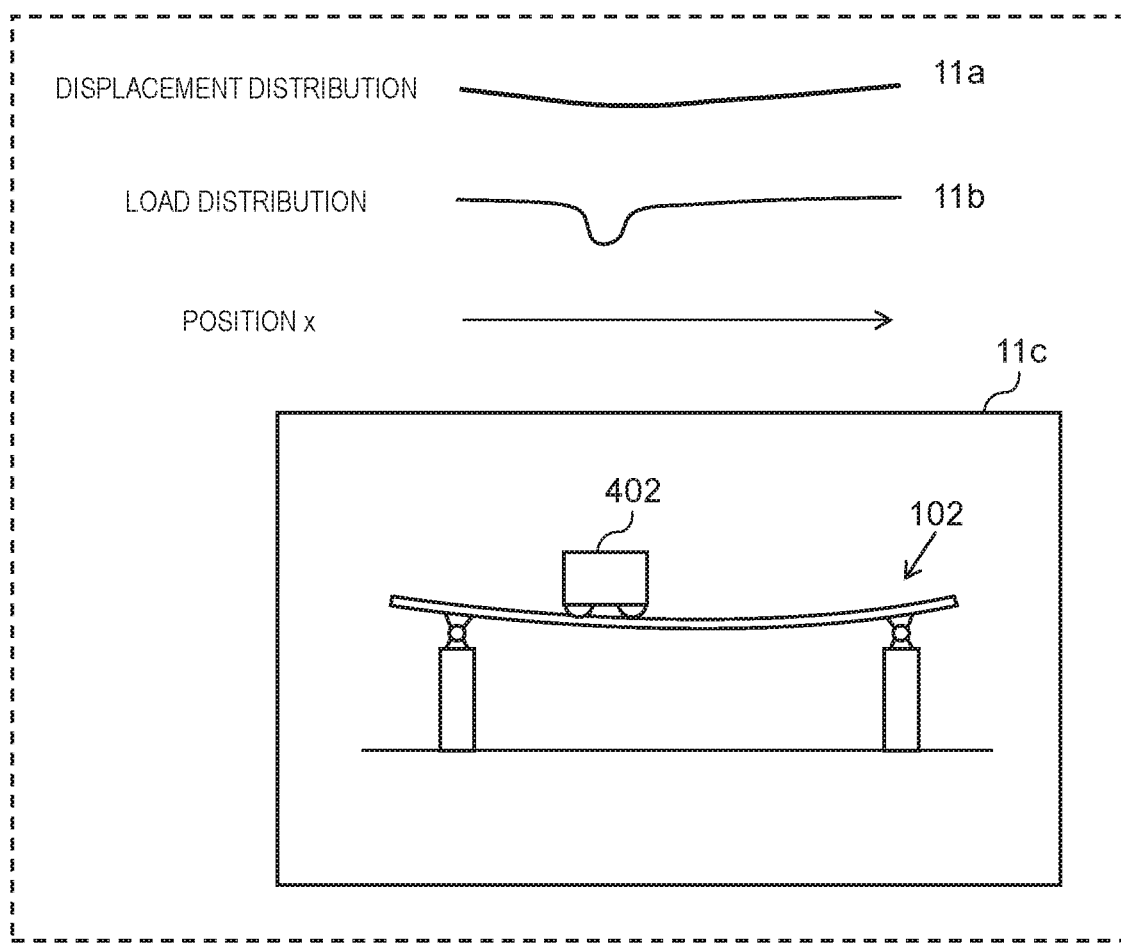
FIG. 11 illustrates another example of the displacement distribution and the load distribution of the bridge.

Similarly, FIG. 11 illustrates another example of the displacement distribution and the load distribution of the bridge. FIG. 11 illustrates displacement distribution 11a and load distribution 11b obtained from captured image 11c. Captured image 10c and captured image 11c are images of bridge 102 captured at different times. In captured image 11c, vehicle 402 is located on left of a center of bridge 102, and bridge 102 is displaced. Also in this case, displacement distribution 11a shows that a portion where vehicle 402 is located is displaced most. Furthermore, load distribution 11b shows that a load is applied to the portion here vehicle 402 is located.

Rigidity calculator 251 calculates a rigidity distribution by using the displacement distribution and the load distribution calculated by load estimator 240. Rigidity calculator 251 calculates bending rigidity distribution Sb(x), for example, by using a mechanics equation such as formula 3.

$$\frac{d^4 y(x)}{dx^4} = \frac{w(x)}{Sb(x)} \qquad \text{[Formula 3]}$$

In formula 3, x is a lateral position of bridge 102, y(x) is a displacement distribution, and w(x) is a load distribution. Such a differential equation can be numerically solved as described, for example, in Hiroyuki KISU, et al, "A study for identification of bending rigidity of a beam", Transactions of the Japan Society of Mechanical Engineers, Series A, Vol. 70, No. 698, 2004.

In a case where an ill-posed problem occurs due to an insufficient condition such as an insufficient number of measurement points or in a case where a measurement value contains noise, rigidity calculator 251 may calculate rigidity by combining a constraint condition such as formula 4 or formula 5 with formula 3. Formula 4 shows that rigidity does not depend on position x, and formula 5 shows that rigidity changes smoothly spatially.

$$\frac{dSb(x)}{dx} = 0 \qquad \text{[Formula 4]}$$

$$\frac{d^2 Sb(x)}{dx^2} = 0 \qquad \text{[Formula 5]}$$

Figure 12:
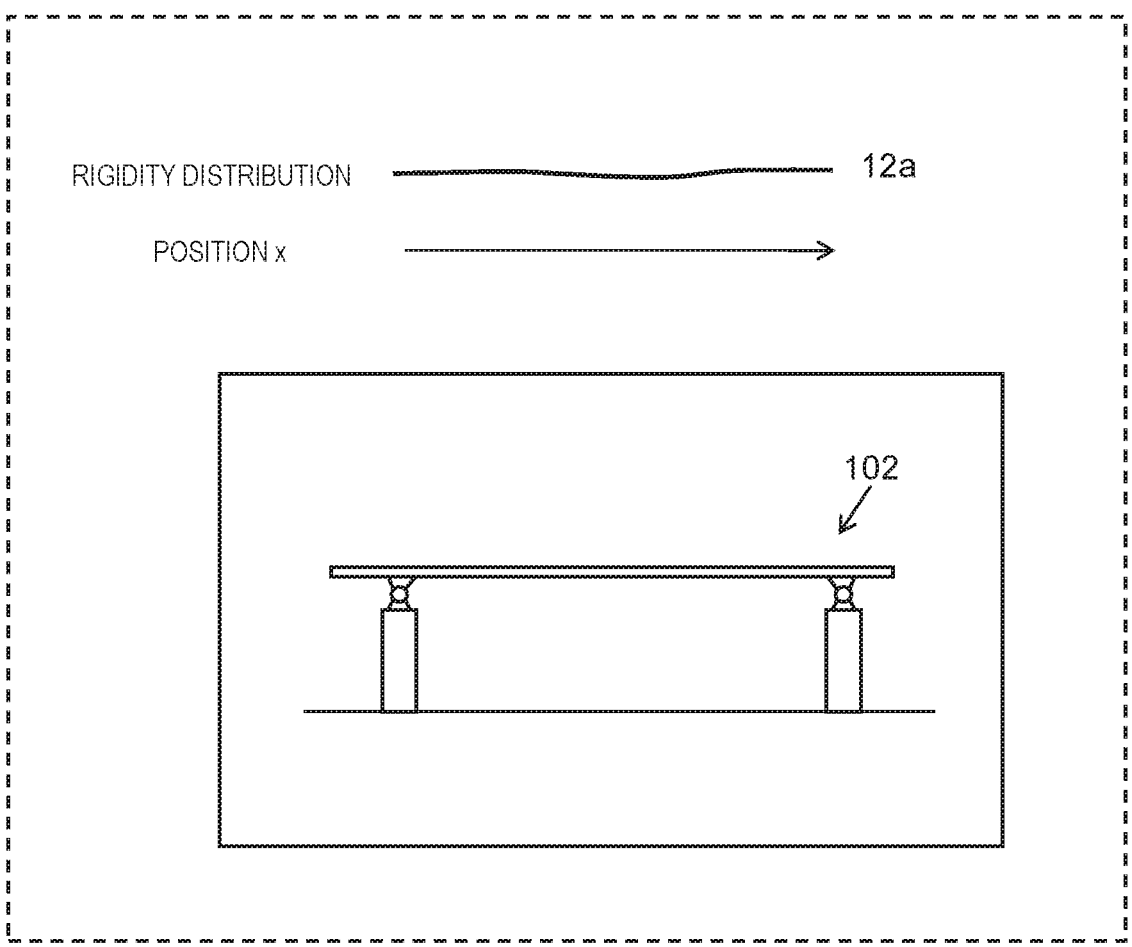
FIG. 12 illustrates an example of the rigidity distribution of the bridge.

FIG. 12 illustrates an example of the rigidity distribution of the bridge. FIG. 12 illustrates rigidity distribution 12a that is constant throughout a whole beam of bridge 102.

Rigidity calculator 251 may use another calculation method of setting evaluation function E(Sb) concerning Sb(x) such as formula 6 as an optimization problem and calculating Sb(x) such that evaluation function E(Sb) is minimized. In formula 6, $|C|^p$ represents p-norm of function C. Furthermore, $\lambda_1$ and $\lambda_2$ are determined in advance as weight parameters.

$$E(Sb) = \left| \frac{d^4 y(x)}{dx^4} - \frac{w(x)}{Sb(x)} \right|^2 + \lambda_1 \left| \frac{dSb(x)}{dx} \right|^1 + \lambda_2 \left| \frac{d^2 Sb(x)}{dx^2} \right|^1 \qquad \text{[Formula 6]}$$

In order to obtain a stable solution in a ease where an ill-posed problem occurs due to an insufficient condition such as an insufficient number of measurement points or in a case where a measurement value contains noise, rigidity calculator 251 may calculate a rigidity distribution by combining displacement distributions and load distributions obtained from a plurality of captured images of same bridge 102 that have different load distributions. For example, rigidity calculator 251 may calculate the rigidity distribution as illustrated in FIG. 12 by combining a plurality of pairs of the displacement distributions and the load distributions at different times as illustrated in FIGS. 10 and 11. In this case, rigidity calculator 251 calculates a common rigidity distribution by utilizing that bridge 102 is same in different captured images. The plurality of captured images having different load distributions can be easily obtained by taking a moving image of bridge 102 while vehicle 402 passes bridge 102. This makes it possible to more accurately obtain a rigidity distribution of bridge 102.

[1-2-4. Operation Example 2]

Next, an example of calculation of shear rigidity Ss(x) is described. In this case, rigidity calculator 251 can calculate a shear rigidity distribution by using a mechanics equation such as formula 7 as in the case of bending rigidity. In formula 7, Sb is bending rigidity.

$$\frac{d^4 y(x)}{dx^4} = \frac{w(x)}{Sb} - \frac{1}{Ss(x)} \frac{d^2 w(x)}{dx^2} \qquad \text{[Formula 7]}$$

[1-2-5. Operation Example 3]

Figure 13:
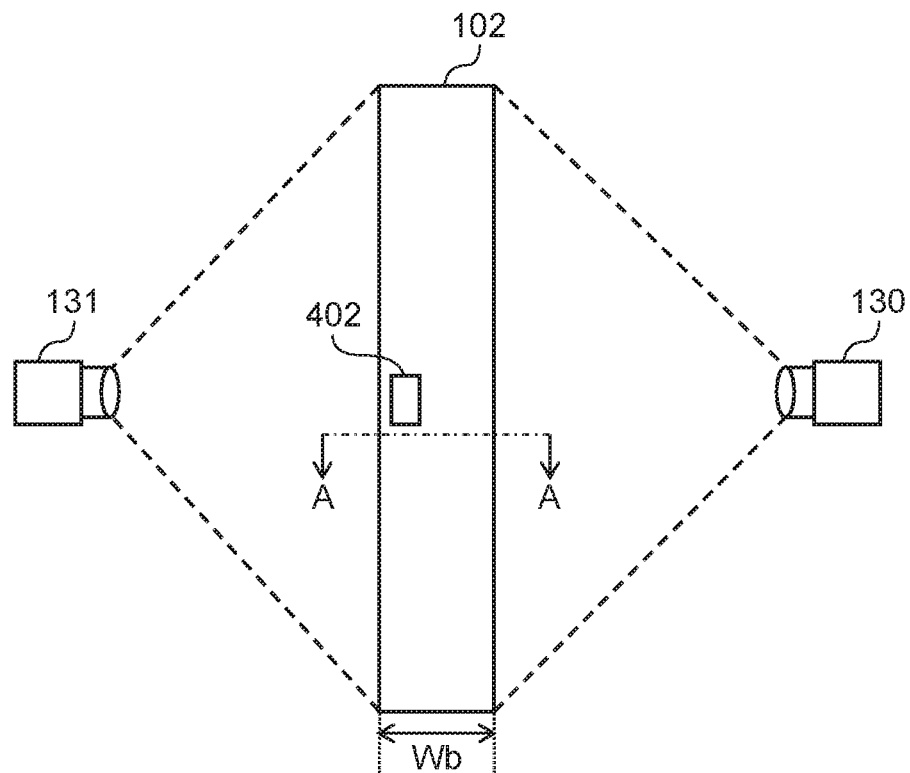
FIG. 13 illustrates an example of a positional relationship between a bridge and imaging devices.
Figure 14:
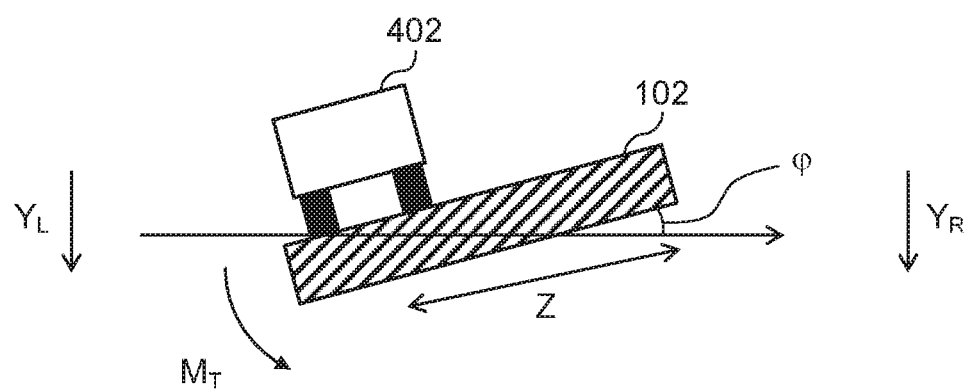
FIG. 14 illustrates a cross section of the bridge.

Next, an example of calculation of torsional rigidity St is described with reference to FIGS. 13 and 14. FIG. 13 illustrates an example of a positional relationship between a bridge and imaging devices. FIG. 14 illustrates a cross section of the bridge. FIG. 14 illustrates a cross section of bridge 102 taken along line A-A in FIG. 13.

In FIG. 13, an upper side is a far side of bridge 102, and a lower side is a near side of bridge 102. It is assumed that vehicle 402 is running from the near side to the far side. Camera 130 captures bridge 102 from a right side in a traveling direction of the vehicle. Camera 131 captures bridge 102 from a left side in the traveling direction of the vehicle. That is, camera 130 (an example of one of a plurality of imaging devices) is disposed on a side opposite to camera 131 (an example of another one of the plurality of imaging devices) across bridge 102.

FIG. 14 illustrates a state where bridge 102 is twisted. More specifically, bridge 102 is twisted by a torsional angle φ due to torsional moment $M_T$ caused by a load of vehicle 402. In FIG. 14, displacement $Y_L$ and displacement $Y_R$ are displacements that occur at a left end and a right end of bridge 102 due to the load of vehicle 402, respectively. Displacement calculator 230 calculates displacement $Y_R$ and displacement $Y_L$ from images captured by camera 130 and camera 131, respectively.

Rigidity calculator 251 can calculate torsional rigidity St by using formula 8.

$$St = \frac{M_T}{\varphi} \qquad \text{[Formula 8]}$$

Input I/F 210 receives input of two captured images of bridge 102 that are captured in synchronization by camera 130 and camera 131. Camera 130 and camera 131 are disposed on both sides of bridge 102 along a direction (a direction parallel with line A-A) orthogonal to a bridge axis as illustrated in FIG. 13. Displacement calculator 230 calculates displacement distribution $y_R(x)$ from the captured image generated by camera 130 and calculates displacement distribution $y_L(x)$ from the captured image generated by camera 131. Displacement calculator 230 calculates torsional angle φ of bridge 102 by using $y_R(x)$, $y_L(x)$, and formula 9. In formula 9, Wb is a width of bridge 102, which is known.

$$\varphi(x) = \arctan\left(\frac{y_R(x) - y_L(x)}{W_b}\right) \qquad \text{[Formula 9]}$$

Furthermore, load estimator 240 finds position z of vehicle 402 in a direction orthogonal to the bridge axis by determining a lane on which vehicle 402 is traveling based on the image showing traveling vehicle 402. It is assumed that a position of the lane in a height direction is known. In this case, load estimator 240 calculates torsional moment $M_T$ by using load position z×load w×gravitational acceleration g.

[1-2-6. Operation Example 4]

Next, a case where axial rigidity Sa of a vertical cable of bridge 112 having a suspension structure is described with reference to FIGS. 15A through 15D.

Figure 15A:
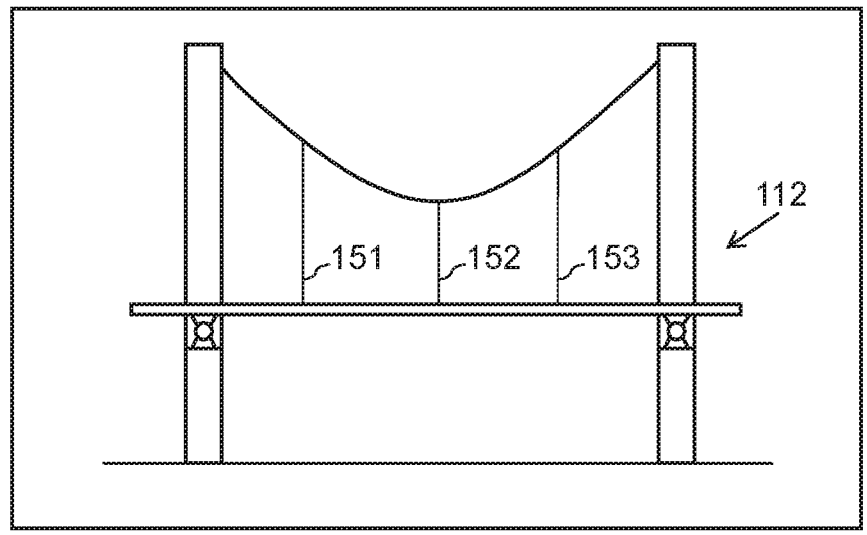
FIG. 15A illustrates another example of the captured image of a bridge.

FIG. 15A illustrates another example of a captured image of a bridge. As illustrated in FIG. 15A, bridge 112 has a suspension structure and includes three vertical cables 151 through 153.

Figure 15B:
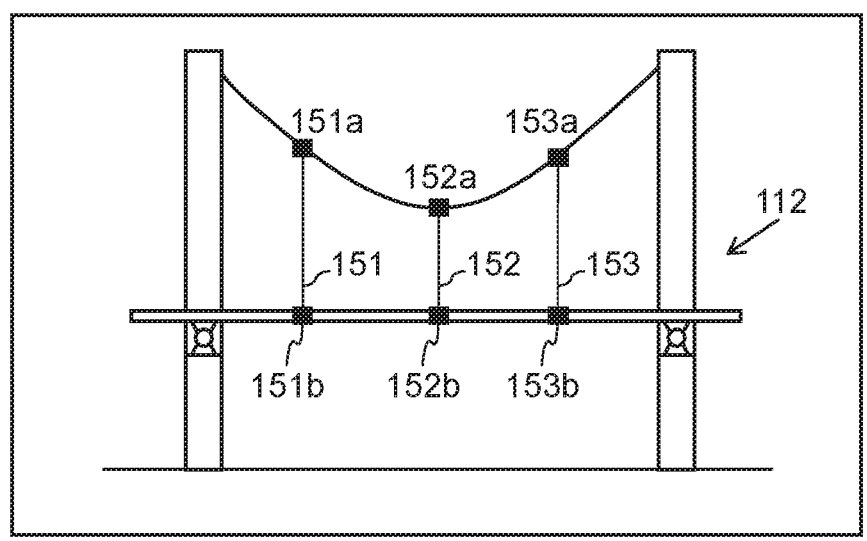
FIG. 15B illustrates another example of the way in which measurement points set on the bridge are disposed.

FIG. 15B illustrates another example of the way in which measurement points set on the bridge are disposed. As illustrated in 15B, both end points of the vertical cables are set as measurement points 151a, 151b, 152a, 152b, 153a, and 153b.

Figure 15C:
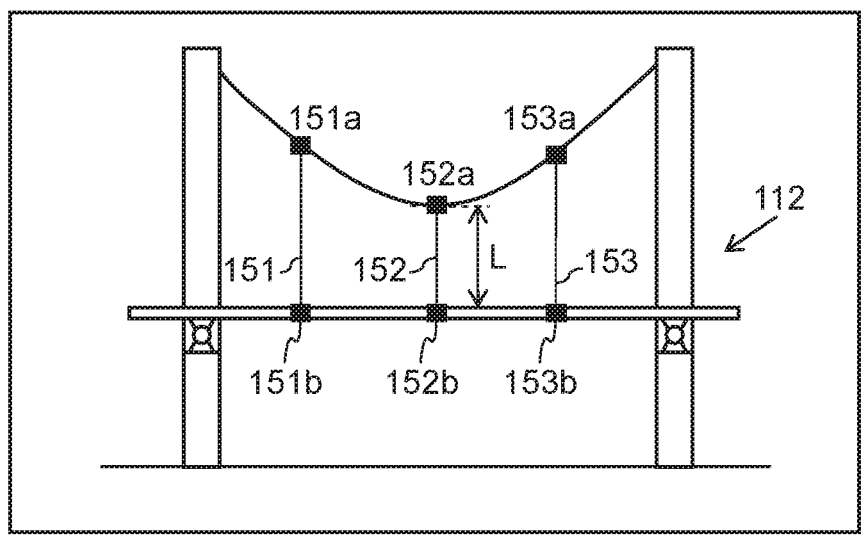
FIG. 15C illustrates a cable length of the bridge.

FIG. 15C illustrates a cable length of the bridge, FIG. 15C illustrates a case where no load is applied to bridge 112. FIG. 15C shows that the cable length of vertical cable 152 is L.

Figure 15D:
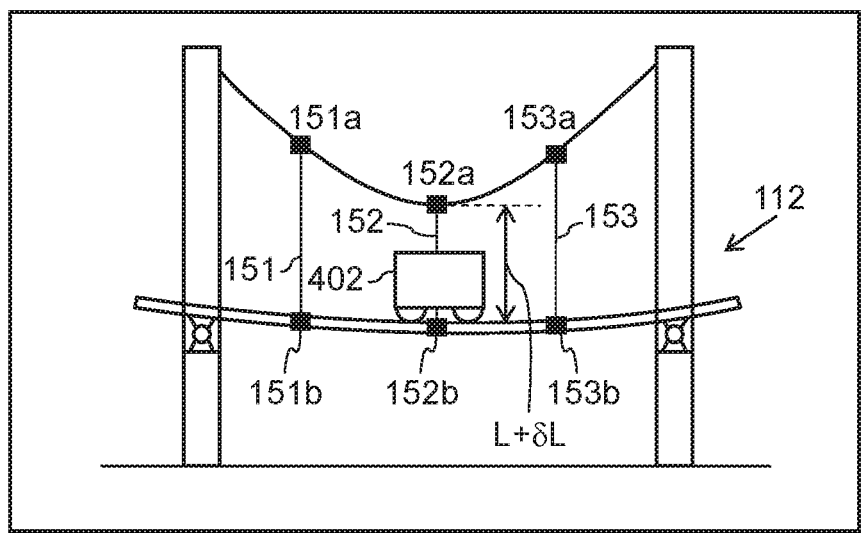
FIG. 15D illustrates another state of the cable length of the bridge.

FIG. 15D illustrates another state of a cable length of the bridge. FIG. 15D illustrates a state where a load is applied to bridge 112 by vehicle 402 running on bridge 112. FIG. 15D shows that bridge 112 is warped due to the load of vehicle 402 and a length of vertical cable 152 becomes L±δL.

In this case, rigidity calculator 251 can calculate axial rigidity Sa of vertical cable 152 by formula 10. In formula 10, N is force applied to vertical cable 152 by the load and is calculated by load w of vehicle 402×gravitational acceleration g. δL is an amount of elongation of a cable length of vertical cable 152 that occurs due to load w. δL is a difference in displacement between measurement points 152a and 152b. δL can be calculated in a similar manner as for vertical cables 151 and 153.

$$Sa = \frac{N}{\delta L} \qquad \text{[Formula 10]}$$

A similar method can be applied not only in a case where a rigidity distribution of a bridge support having a suspension structure is calculated, but also in a case where a rigidity distribution of a whole complex structure such as a cable-stayed bridge, a harp bridge, an electric wire having a cable structure, or a steel tower is calculated.

Although examples of calculation of bending rigidity, shear rigidity, torsional rigidity, and axial rigidity have been described in the first exemplary embodiment, it is unnecessary to calculate all of these. It is unnecessary to calculate a rigidity parameter that can be ignored in advance or an unnecessary rigidity parameter. Furthermore, a mechanics equation used for calculation of rigidity may be simpler than the above formula or may be stricter than the above formula. Furthermore, a mechanics equation including a plurality of kinds of rigidity measurement may be used.

[1-3. Effects and Other Benefits]

As described above, rigidity measurement apparatus 200 according to the present exemplary embodiment is a rigidity measurement apparatus that measures rigidity of an object to be measured and includes load estimator 240, displacement calculator 230, and rigidity calculator 250. Load estimator 240 estimates a load applied to a measurement point set on bridge 102 by using a captured image of bridge 102. Displacement calculator 230 calculates a displacement of a measurement point by using the captured images. Rigidity calculator 250 calculates rigidity of bridge 102 by using the load and the displacement.

This makes it possible to remotely measure rigidity of an object to be measured.

Furthermore, load estimator 240 calculates a load distribution of bridge 102 by estimating loads applied to a plurality of measurement points set on bridge 102. Displacement calculator 230 calculates a displacement distribution of bridge 102 by calculating displacements of the plurality of measurement points. Rigidity calculator 250 calculates a rigidity distribution of bridge 102 by using the load distribution and the displacement distribution.

This makes it possible to remotely measure a rigidity distribution of a whole object to be measured.

It is therefore possible to acquire a displacement distribution and a load distribution of a whole structure of an object to be measured and thereby calculate a rigidity distribution of the whole structure of the object to be measured easily at low cost. This makes it possible to easily obtain strength evaluation of a structure. Furthermore, since an image is recorded, a state of appearance of an object to be measured can also be grasped easily.

Furthermore, since camera 101 captures a wide range including measurement points and a reference measurement point on an object to be measured, rigidity of the object to be measured can be measured with high accuracy while keeping influence of camera shake small.

Second Exemplary Embodiment

A second exemplary embodiment is described below with reference to FIGS. 1 through 3, FIG. 7, and FIGS. 16 through 19B.

Bridge 102 is not always located at a same position in a plurality of captured images generated by imaging device 101. In such a case, if a coordinate position of a measurement point set on one captured image is applied to another captured image, there is a possibility that the applied position of the measurement point be deviated from an originally set position. Accordingly displacement calculator 230 calculates a displacement between deviated measurement points. In order to address this, rigidity measurement apparatus 202 according to the second exemplary embodiment includes setting unit 280. Setting unit 280 sets a position of a measurement point of an object to be measured in a captured image for which a displacement is to be calculated by referring to a position of a measurement point on the object to be measured set in another captured image.

[2-1. Configuration]

Figure 16:
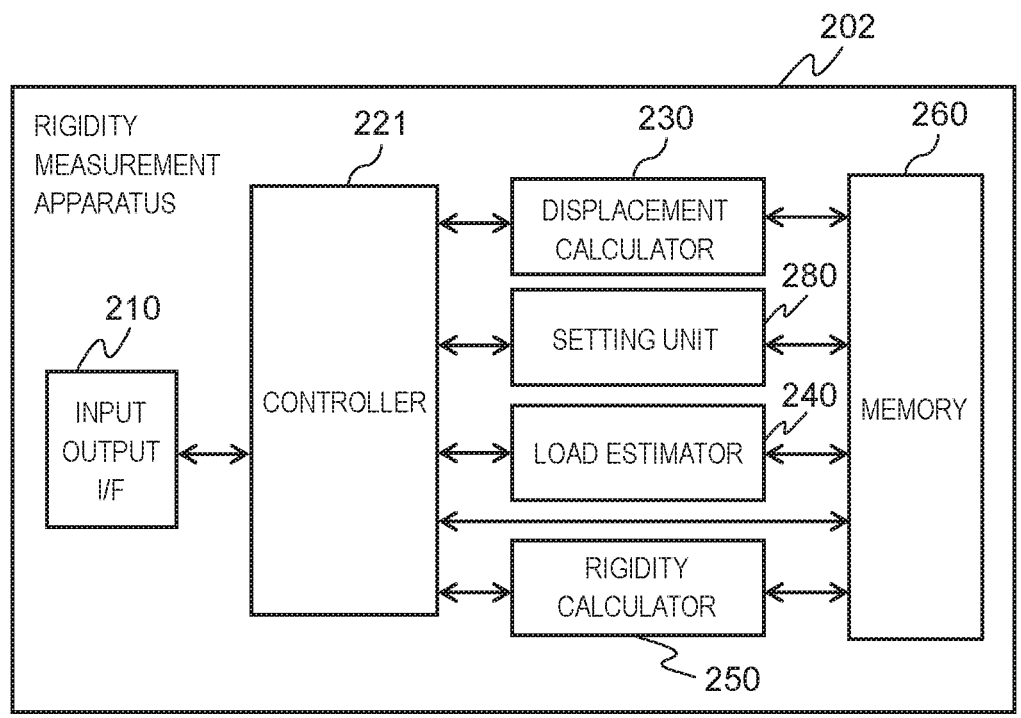
FIG. 16 is a block diagram illustrating an example of a configuration of a rigidity measurement apparatus according to a second exemplary embodiment.

FIG. 16 is a block diagram illustrating an example of a configuration of rigidity measurement apparatus 202 according to the second exemplary embodiment. In FIG. 16, constituent elements that perform identical operations to FIG. 2 are given identical reference signs and are not described repeatedly.

Rigidity measurement apparatus 202 according to the second exemplary embodiment includes setting unit 280 that sets a measurement point in addition to the configuration of rigidity measurement apparatus 200 according to the first exemplary embodiment.

Setting unit 280 sets a measurement point based on an object to be measured. In other words, setting unit 280 sets a measurement point of bridge 102 in a first captured image based on a measurement point set on bridge 102 in a second captured image. In the present exemplary embodiment, it is assumed that an image-capturing position of imaging device 101 at a time of capturing of the first captured image and an image-capturing position of imaging device 101 at a time of capturing of the second captured image are different. Note that the present exemplary embodiment is also applicable even in a case where the first captured image and the second captured image are captured in reverse order.

[2-2. Operation]

Rigidity measurement apparatus 200 according to the first exemplary embodiment and rigidity measurement apparatus 202 according to the second exemplary embodiment are different only in terms of an operation for setting a measurement point performed by setting unit 280, and therefore only an operation of setting unit 280 is described.

In the second exemplary embodiment, the first captured image for which a displacement is to be calculated is captured image 500 of FIG. 7.

Figure 17:
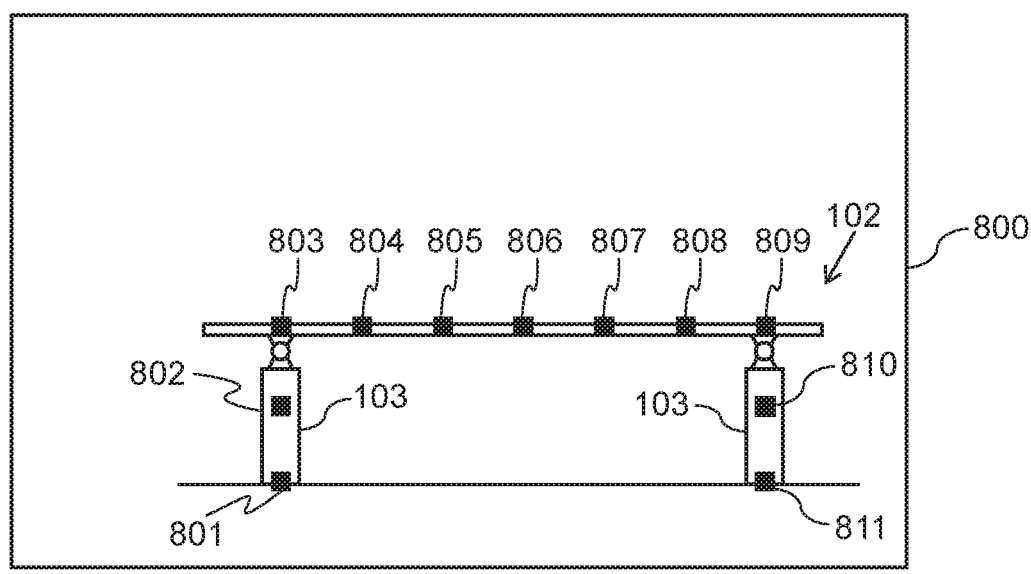
FIG. 17 illustrates an example of a captured image of a bridge according to the second exemplary embodiment.

FIG. 17 illustrates an example of the second captured image of bridge 102 according to the second exemplary embodiment. FIG. 17 illustrates captured image 800 and an example of a way in which measurement points set on bridge 102 in captured image 800 are disposed. Captured image 500 and captured image 800 are images of bridge 102 captured from different positions.

In FIG. 17, measurement points 801 through 811 are measurement points set on bridge 102. Measurement points 801 through 811 may be set in advance by a user or may be automatically set on bridge 102 after image recognition of bridge 102 as in the first exemplary embodiment.

It is assumed that a position of bridge 102 in captured image 800 is deviated toward a lower right side relative to a position of bridge 102 in captured image 500 as illustrated in FIGS. 7 and 17. In a case where a position of a captured object to be measured is deviated between a plurality of captured images of the same object to be measured as described above, there is a possibility that positions of measurement points set on bridge 102 be deviated (different) between the captured images.

In view of this, in the second exemplary embodiment, setting unit 280 sets measurement points 501 through 511 (including a reference measurement point) on bridge 102 in captured image 500 of FIG. 7 based on captured image 800 and positions of measurement points 801 through 811 (including a reference measurement point).

Specifically, setting unit 280 determines the positions of the measurement points in captured image 500 that correspond to the measurement points of captured image 800 by using local features of an image, block matching, a correlation method, or the like. As the local features, scale-invariant feature transform (SIFT), speeded up robust features (SURF), or the like can be used.

Figure 18:
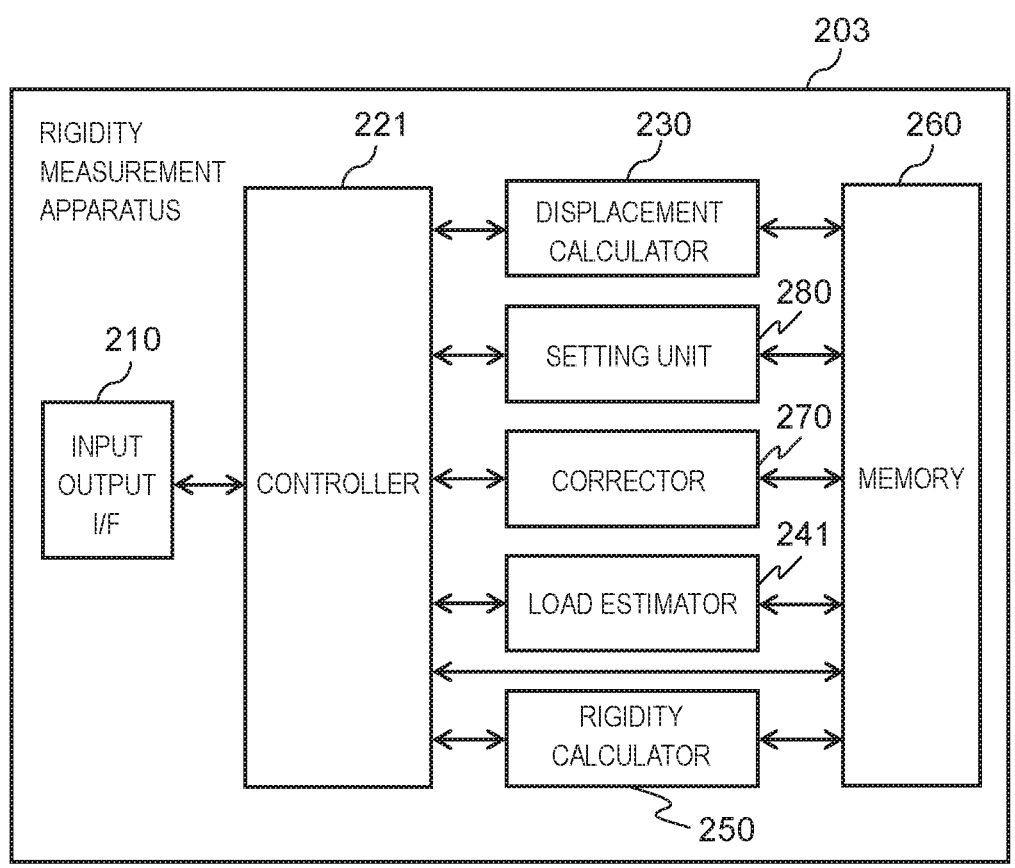
FIG. 18 is a block diagram illustrating another example of the configuration of the rigidity measurement apparatus according to the second exemplary embodiment.

Rigidity measurement apparatus 202 according to the second exemplary embodiment may include corrector 270 (see rigidity measurement apparatus 203 of FIG. 18) as in the first exemplary embodiment. FIG. 18 is a block diagram illustrating another example of a configuration of a rigidity measurement apparatus according to the second exemplary embodiment.

[2-3. Effects and Other Benefits]

As described above, rigidity measurement apparatus 202 according to the second exemplary embodiment further includes setting unit 280. Setting unit 280 sets a measurement point based on bridge 102.

This makes it possible to calculate a displacement at a same position on an object to be measured in a case where an object to be measured that as measured in past is measured again.

Accordingly, when a same object to be measured is captured again, measurement points in a captured image are set based on the object to be measured in a case where an image-capturing position or an imaging device changes. It is therefore possible to reduce trouble of setting a large umber of measurement points again. That is, it is possible to easily make comparison between measurement results of the object to be measured captured at different times.

The present disclosure is also applicable, for example, even in a case where a posture of an imaging device changes when an object to be measured is captured plural times within a predetermined period.

Other Exemplary Embodiments

The first and second exemplary embodiments have been described above as an illustration of the technique disclosed in the present application. However the technique of the present disclosure is not limited thereto, and can be also applied to exemplary embodiments in which changes, replacements, additions, omissions, and the like are made. Additionally, constituent elements described in the above exemplary embodiments can be combined to configure a new exemplary embodiment.

Hence, other exemplary embodiments are illustrated below.

Camera 101 may be provided separately from rigidity measurement apparatus 200 as illustrated in FIG. 1 or may be provided in rigidity measurement apparatus 200. A captured image may be a monochromatic image or may be a color image (including a multi spectral image). Camera 101 need not be a typical camera. Camera 101 may be a camera that detects an object to be measured by using a distance measuring sensor or an acceleration sensor and output array data obtained by detection as an image.

In the above exemplary embodiments, a single camera is mainly used, but a plurality of cameras that capture different places of a same object to be measured may be used as illustrated in FIG. 13. In this case, the processes to step S330 are performed for each of captured images generated by the plurality of cameras by using captured images captured in synchronization by the plurality of cameras. In step S340 and subsequent steps, similar processes can be performed by using all displacement distributions obtained from the plurality of captured images as a combination. This makes it possible to accurately measure a displacement of an object to be measured that cannot be captured by a single camera. That is, displacement calculator 230 may calculate a displacement by using a plurality of captured images of object to be measured 102 captured in synchronization by the plurality of imaging devices.

In the above exemplary embodiments, two-dimensional displacement $Di(x, y)$ is calculated, but three-dimensional displacement $Di(x, y, z)$ may be calculated by acquiring a depth image. A high-accuracy three-dimensional displacement can be obtained by performing a similar procedure to the above exemplary embodiments after displacement calculation. As a camera or a method for generating the depth image, a stereo camera for synchronized capturing using a plurality of cameras, a multi-view camera stereo method, a pattern projection method, a time-of-fight (TOF) camera, a laser displacement gauge, or the like can be used. That is, displacement calculator 230 may calculate a displacement by using a depth image including information indicative of a distance between a measurement point and an imaging device that captures an object to be measured.

Although bridge 102 is illustrated as an example as an object to be measured in the above exemplary embodiments, similar effects can also be obtained even in a case where a construction such as a building, a steel tower, a chimney, a wall surface, a floor material, a plate material, a steel scaffolding, a road surface, a railway track, or a vehicle body is used as the object to be measured.

Furthermore, light captured by camera 101 may be ultraviolet ray, near infrared ray, or far infrared ray as well as visible light.

Figure 20:
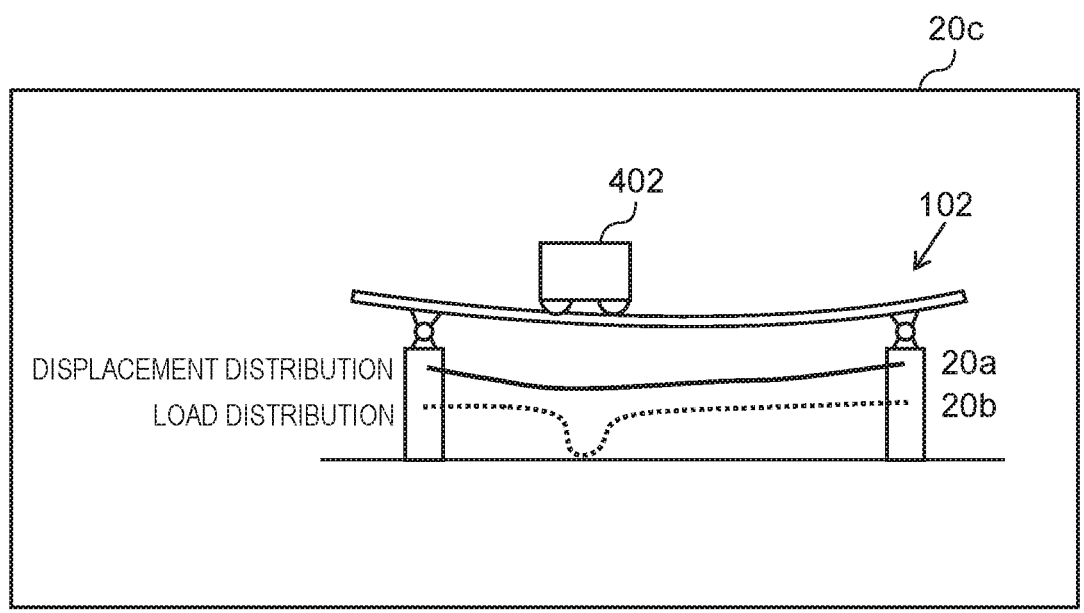
FIG. 20 illustrates an example of a result of visualization of displacement distribution and a load distribution.

Furthermore, a rigidity distribution calculated by rigidity calculator 250 may be visualized. For example, controller 220 (an example of a superimposed image generator) may generate a superimposed image by superimposing an image based on rigidity calculated by rigidity calculator 250 on at least one of a plurality of captured images. Similarly, controller 220 may visualize displacement distribution 20a calculated by displacement calculator 230 or load distribution 20b calculated by load estimator 240 by superimposing displacement distribution 20a or load distribution 20b on captured image 20c, as illustrated in FIG. 20. This allows a user to check an operation of rigidity measurement apparatus 200. It is unnecessary to display all of a displacement distribution, a load distribution, and a rigidity distribution, and it is only necessary to display only a necessary distribution.

Figure 19A:
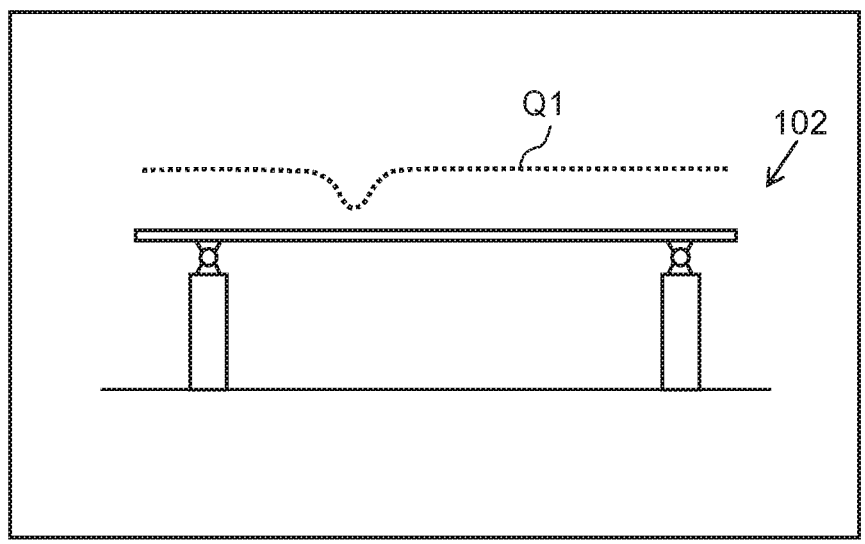
FIG. 19A illustrates an example of visualization of a rigidity distribution.

Controller 220 generates a superimposed image by superimposing an image based on a rigidity distribution on a captured image of bridge 102, as illustrated in FIG. 19A. In FIG. 19A, broken line Q1 indicates a rigidity distribution displayed in accordance with a position of bridge 102. In FIG. 19A, a part of broken line Q1 depressed downward indicates that rigidity of part of bridge 102 has decreased. A rigidity distribution may be expressed not only by using a graph, but also by gradation or colors. By displaying a rigidity distribution in this way, a spatial distribution of rigidity of bridge 102 can be easily grasped. In a case where a depth image is used, similar ways of display can be achieved by using 3D display.

Figure 19B:
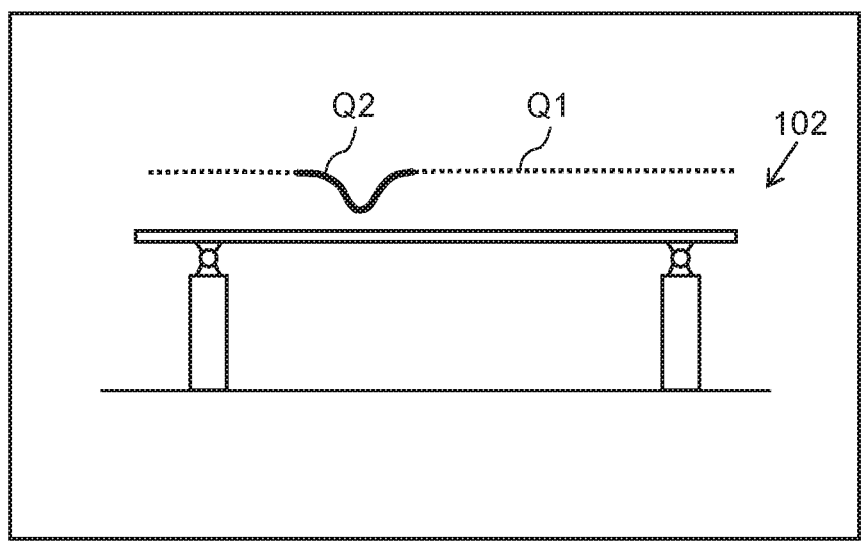
FIG. 19B illustrates an example of a result in a case where it is determined that there is abnormality.

Furthermore, rigidity calculator 250 may store a reference value of rigidity of an object to be measured and determine whether or not calculated rigidity is abnormal by using the reference value. Rigidity calculator 250 determines that rigidity is abnormal, for example, in a case where the calculated rigidity is equal to or smaller than the reference value. Controller 220 may visualize not only a rigidity distribution, but also a position of rigidity determined to be abnormal by rigidity calculator 250, as illustrated in FIG. 19B. In FIG. 19B, the position of the abnormal rigidity is indicated by thick line Q2. That is, rigidity calculator 250 may output a result of determination as to whether or not rigidity is abnormal.

Furthermore, displacement calculator 230 may estimate a displacement of a point other than a measurement point by spatially interpolating calculated displacements of a whole object to be measured. Furthermore, corrector 270 may correct a captured image or a displacement calculated by displacement calculator 230 such that actual scales of an object to be measured included in captured images become equal. In a case where captured image is corrected, corrector 270 performs correction before displacement calculator 230 calculates a displacement.

Furthermore, rigidity calculator 250 may calculate a rigidity distribution by combining a plurality of different load distributions and displacement distributions corresponding to the load distributions.

It should be noted that, since the aforementioned exemplary embodiments illustrate a technique of the present disclosure, various changes, replacements, additions, omissions, and the like can be made the claims and their equivalents.

INDUSTRIAL APPLICABILITY

A rigidity measurement apparatus according to the present disclosure is applicable, for example, to gauging, measurement, analysis, diagnosis, and inspection of structural strength of a structure.

REFERENCE MARKS IN THE DRAWINGS

1: rigidity measurement system
101, 130, 131: camera aging device
102, 112: bridge (object to be measured)
200, 201, 202, 203: rigidity measurement apparatus 210: input output I/F
220, 221: controller
230: displacement calculator
240: load estimator
250, 251: rigidity calculator
260: memory
270: corrector
280: setting unit

The invention claimed is:

1. A rigidity measurement apparatus that measures rigidity of an object to be measured, the rigidity measurement apparatus comprising:
   a load estimator that estimates a load applied to a measurement point set on the object to be measured by using a captured image of the object to be measured;
   a displacement calculator that calculates a displacement of the measurement point by using the captured image;
   a rigidity calculator that calculates the rigidity of the object to be measured by using the load and the displacement; and
   a setting unit that sets the measurement point based on the object to be measured.

2. The rigidity measurement apparatus according to claim 1, further comprising
   a memory in which a load value of a load source is stored,
   wherein the load estimator is configured to detect a position of the load source on the object to be measured by using the captured image, and to estimate the load applied to the measurement point by using the load value and the position of the load source.

3. The rigidity measurement apparatus according to claim 1, further comprising
   a memory in which a load value corresponding to a kind of a load source is to be stored,
   wherein the load estimator is configured to detect a position and the kind of the load source on the object to be measured by using the captured image, and to estimate the load applied to the measurement point by using the load value corresponding to the kind of the load source and the position of the load source.

4. The rigidity measurement apparatus according to claim 1, further comprising
   a memory in which a predetermined load value is stored,
   wherein the load estimator is configured to detect a position of a load source on the object to be measured by using the captured image, and to estimate the load applied to the measurement point by using the predetermined load value and the position of the load source.

5. The rigidity measurement apparatus according to claim 1,
   wherein the captured image includes information indicative of a distance between the measurement point and an imaging device that captures the object to be measured, and
   wherein the displacement calculator is configured to calculate the displacement by using the captured image.

6. The rigidity measurement apparatus according to claim 1, further comprising:
   a corrector,
   wherein the displacement calculator is configured to calculate a reference displacement of a predetermined reference measurement point,
   wherein the corrector is configured to correct the displacement by using the reference displacement, and
   wherein the rigidity calculator is configured to calculate the rigidity by using the corrected displacement.

7. The rigidity measurement apparatus according to claim 1,
   wherein the displacement calculator is configured to calculate the displacement by using block matching or a correlation method.

8. The rigidity measurement apparatus according to claim 1,
   wherein the load estimator is configured to calculate a load distribution of the object to be measured by estimating a plurality of the loads applied to a plurality of the measurement points set on the object to be measured,
   wherein the displacement calculator is configured to calculate a displacement distribution of the object to be measured by calculating a plurality of the displacements of the plurality of measurement points, and
   wherein the rigidity calculator is configured to calculate a rigidity distribution of the object to be measured by using the load distribution and the displacement distribution.

9. The rigidity measurement apparatus according to claim 8,
   wherein the rigidity calculator is configured to calculate the rigidity distribution by combining a plurality of the load distributions that are different from one another and a plurality of the displacement distributions corresponding to the plurality of the load distributions.

10. The rigidity measurement apparatus according to claim 1, further comprising
    a superimposed image generator that generates a superimposed image by superimposing an image based on the rigidity on the captured image.

11. The rigidity measurement apparatus according to claim 1,
    wherein the rigidity calculator is configured to store a reference value of rigidity of the object to be measured, determines whether or not the calculated rigidity is abnormal by using the reference value, and outputs a result of the determination.

12. The rigidity measurement apparatus according to claim 11, further comprising
    a superimposed image generator that generates a superimposed image by superimposing an image based on the rigidity on the captured image,
    wherein the superimposed image generator is configured to visualize the rigidity determined to be abnormal by the rigidity calculator in the superimposed image.

13. The rigidity measurement apparatus according to claim 1, further comprising
    a scaling unit that performs scale correction of the displacement based on a distance between the measurement point and an imaging device that captures the object to be measured.

14. The rigidity measurement apparatus according to claim 1,
    wherein the displacement calculator is configured to calculate the displacement by using a plurality of the captured images of the object to be measured that are captured in synchronization by a plurality of imaging devices.

15. The rigidity measurement apparatus according to claim 14,
    wherein one of the plurality of imaging devices is disposed on a side opposite to another one of the plurality of imaging devices across the object to be measured.

16. A rigidity measurement method for measuring rigidity of an object to be measured, the rigidity measurement method comprising:
- estimating a load applied to a measurement point set on the object to be measured by using a captured image of the object to be measured;
- calculating a displacement of the measurement point by using the captured image;
- calculating the rigidity of the object to be measured by using the load and the displacement; and
- setting the measurement point based on the object to be measured.

* * * * *